(12) United States Patent
Sournac et al.

(10) Patent No.: US 8,246,685 B2
(45) Date of Patent: Aug. 21, 2012

(54) VERTEBRAL DISC PROSTHESIS, NOTABLY FOR CERVICAL VERTEBRAE

(75) Inventors: Denys Sournac, Reyrieux (FR); David Ryan, Collonges au Mont d'Or (FR)

(73) Assignee: Medicrea International, Neyron (FR)

( * ) Notice: Subject to any disclaimer, the term of this patent is extended or adjusted under 35 U.S.C. 154(b) by 166 days.

(21) Appl. No.: 12/746,102

(22) PCT Filed: Dec. 2, 2008

(86) PCT No.: PCT/IB2008/055048
§ 371 (c)(1),
(2), (4) Date: Jun. 3, 2010

(87) PCT Pub. No.: WO2009/074915
PCT Pub. Date: Jun. 18, 2009

(65) Prior Publication Data
US 2010/0256763 A1    Oct. 7, 2010

(30) Foreign Application Priority Data
Dec. 12, 2007    (FR) ...................................... 07 08655

(51) Int. Cl.
*A61F 2/44*    (2006.01)
(52) U.S. Cl. .................................. 623/17.16; 623/17.11

(58) Field of Classification Search .... 623/17.11–17.16; 606/249
See application file for complete search history.

(56) References Cited

U.S. PATENT DOCUMENTS

| | | | |
|---|---|---|---|
| 6,063,121 A | 5/2000 | Xavier | |
| 2002/0128715 A1* | 9/2002 | Bryan et al. | 623/17.15 |
| 2003/0135278 A1 | 7/2003 | Eckman | |
| 2003/0233146 A1* | 12/2003 | Grinberg et al. | 623/17.14 |
| 2004/0024460 A1 | 2/2004 | Ferree | |
| 2005/0113927 A1 | 5/2005 | Malek | |

FOREIGN PATENT DOCUMENTS

| | | |
|---|---|---|
| WO | WO 03/007779 A | 1/2003 |
| WO | WO 2004/028415 A | 4/2004 |

* cited by examiner

*Primary Examiner* — Kevin T Truong
*Assistant Examiner* — Larry E Waggle, Jr.
(74) *Attorney, Agent, or Firm* — Defillo & Associates, Inc; Evelyn A. Defillo

(57) ABSTRACT

The present invention relates to a prosthesis including a first component that delimits a single central housing, including a bottom forming a first articular surface, a peripheral wall and, at a distance from the bottom, an edge extending inwards, a peripheral supporting surface, and on the side turned towards said bottom a second articular surface; and a second component including a plate intended to come into contact with the vertebral plate of the relevant vertebra and a single central pin with a widened head.

10 Claims, 2 Drawing Sheets

VERTEBRAL DISC PROSTHESIS, NOTABLY FOR CERVICAL VERTEBRAE

This application is a national stage entry of PCT/IB2008/055048 filed Dec. 2, 2008, under the International Convention claiming priority over French Application No. 0708655 filed Dec. 12, 2007.

FIELD OF THE INVENTION

The present invention relates to a vertebral disc prosthesis notably for cervical vertebrae.

BACKGROUND OF THE INVENTION

Producing disc prostheses in two or three components with which the movements of the vertebrae may be reproduced is known. When the prosthesis comprises two components, these components comprise complementary articular surfaces, providing direct jointing of one component with the other. When the prosthesis comprises three components, both components anchored at the respective vertebrae are each jointed on an intermediate sliding component, generally in polyethylene.

The existing vertebral disc prostheses, particularly those intended for cervical vertebrae, do not give complete satisfaction. Indeed, the repeated movements which they undergo, result in more or less rapid wear of the articular surfaces, which in the case of cervical disc prostheses have reduced dimensions. This wear leads to an undesirable diffusion of particles into the organism of the patient.

When the prosthesis comprises three components, there moreover exists a risk of expulsion of the intermediate component.

Further, the existing prostheses are relatively complex to make, taking into account stresses resulting from metal/metal or metal/polyethylene contacts.

Document US 2004/024460 describes a disc prosthesis comprising rigid components and a damping component interposed between these rigid components. The damping component is central and the rigid components comprise several sets of peripheral or lateral "cylinders", indicated as reducing the tiltability of a rigid component relatively to the other. FIG. 11B shows a possibility for the "pistons" of the "cylinders" of abutting against the bottom of the "cylinders", causing the damping component to achieve partial damping, whereas FIG. 11C shows a possibility for the "pistons" of the "cylinders" of not abutting against the bottom of the "cylinders", causing the damping component to achieve total damping. FIGS. 22a and 22b of this document show a version of the disc illustrated in FIG. 11, in which the pistons comprise widened heads, and cylinders form internal edges, in order to form the limiting travel abutments.

SUMMARY OF THE INVENTION

The object of the present invention is to find a remedy to the whole of the drawbacks of existing prostheses.

Its main goal is therefore to provide a vertebral disc prosthesis notably for cervical vertebrae, wherein wear of the articular surfaces remains reduced.

Another goal of the invention is to provide a prosthesis which does not induce any risk of expulsion of an intermediate component.

An additional goal of the invention is to provide a prosthesis which is simpler to make than the existing prostheses.

The relevant prosthesis comprises, in a way known per se, two components intended to be connected to the respective vertebral plates, which are jointed to each other.

According to the invention, a first of these two components comprises a bottom, a peripheral wall and at a distance from said bottom, an edge extended inwards, which delimits between them a single central housing, said bottom forming a first articular surface, and said edge forming on the opposite side to said bottom, a peripheral supporting surface and, on the side turned towards said bottom, a second articular surface;

the second component comprises a plate intended to come into contact with the vertebral plate of the relevant vertebra and a single central pin with a widened head, this head forming at its free end, a third articular surface able to cooperate with said first articular surface, and, on its side turned to the side of said plate, a fourth articular surface able to cooperate with said second articular surface;

said housing and said head are mutually dimensioned so that said first and second components are mobile relatively to each other, sideways, i.e. perpendicularly to the axis of said central pin, and axially with respect to each other, i.e. along the axis of this central pin;

the prosthesis comprises at least one component in an elastically deformable material, interposed between said peripheral supporting surface of the first component and said plate of the second component, this component in an elastically deformable material normally maintaining said second and fourth articular surfaces in contact with each other and being able to be compressed so that said first and third articular surfaces will come into contact with each other.

The prosthesis according to the invention thereby combines jointed components with dual pairs of articular surfaces and at least one component in an elastically deformable material, normally maintaining said second and fourth supporting surfaces in contact with each other. In the case of a force being exerted axially on the prosthesis, the component is elastically compressed within the limit of the coming into mutual contact of said first and third articular surfaces. This compression damps this movement of the components and is limited by this coming into contact, thereby eliminating the risk of an excessive stress being exerted on the deformable component, which may lead to deterioration of the latter. In the case of an axially exerted force, but on one side of the prosthesis, the deformable component is only compressed on this side; it thus allows said first and third articular surfaces to come into contact on this same side but, on the opposite side, it maintains the contact of said second and fourth articular surfaces. The surfaces in contact thus remain extensive and the deformation undergone by the deformable component remains limited. In the case of a force tending to displace an component in translation relatively to the other component in a transverse direction relatively to the vertebrae, the deformable component allows the second and fourth articular surfaces to slide on each other on the side opposite to the one on which said force is exerted, while allowing contact of the first and third articular surfaces on the side on which said force is exerted. Here also, the articular surfaces in contact remain large and the deformation of the deformable component only occurs within limits allowed by the possible displacement of first and second components relatively to each other As this is apparent from the foregoing, with the prosthesis according to the invention, a continuity of the articular surfaces may be obtained regardless of the force exerted on the prosthesis, with permanently two articular surfaces in contact. The result of this is lesser wear of the articular surfaces and perfect restoration of the movement of the natural joint.

The invention results from the observation that the existing prostheses are designed in order to produce jointing of the components around a determined single geometrical centre, regardless of whether the prosthesis consists of two or three components. This single geometrical centre is in actual fact not adapted to the complexity of the movements which both components of such a prosthesis may undergo, which leads to the aforementioned premature wear. The prosthesis according to the invention, which may be described as a "semi-stressed" prosthesis, on the contrary, does not define any single jointing centre; by means of the conjugate effects of both pairs of articular surfaces and of the elastically deformable component, this prosthesis provides wide possibilities of movements, adapted to said complex movements.

Preferably, the prosthesis comprises a component in an elastically deformable material in the shape of a ring.

Preferably, said first component comprises, at the border of said supporting surface, an outer retaining edge, dimensioned in order to perform lateral retention of each elastically deformable component.

This edge prevents the risk of displacement of this (these) deformable component(s) with respect to this first component.

Preferably, this outer retaining edge extends over the whole of the periphery of said supporting surface.

With the same purpose, said second component comprises on the side of said plate, a boss coaxial with said pin, dimensioned in order to fittedly receive the elastically deformable component.

According to a preferred embodiment of the invention, said first articular surface is convex and has the shape of a spherical cap, said third articular surface being concave and of a shape complementary to this first articular surface.

Preferably, the head of the pin has a rounded peripheral face connected to said second and fourth articular surfaces through rounded connecting areas, and said first articular surface is connected to said second articular surface though a rounded peripheral area.

These rounded areas contribute to limiting wear experienced by the components.

Said first and second components may be made in metal. Preferably there are made in ceramic, which, in addition to the reduced friction coefficient, allows resolution of different manufacturing and assembling problems which the components of a known prosthesis of this type have.

Preferably, the head of said pin has a non-circular shape allowing it to be engaged into the housing delimited by said first component when said second component is found in a determined angular position relatively to this first component, but preventing this head from coming free out of this housing in any other relative angular position of both components.

Any risk of escape of said pin out of said housing is thereby eliminated.

Notably, said head may comprise two side flats so as to impart said non-circular shape to it.

According to another possibility, said first component may be in two portions, allowing the head of said pin to be easily engaged into the housing delimited by this component when both of these portions are not assembled, and retaining this head in this housing when they are assembled.

Said elastically deformable component may have deformability such that it may be engaged behind said head by simple circumferential stretching. This component may also not have such deformability, in which case the pin may not be firmly attached to said plate upon placement of the component and may be firmly attached to this plate once this placement is achieved.

BRIEF DESCRIPTION OF THE DRAWINGS

The invention will be better understood and other features and advantages thereof will become apparent, with reference to the appended schematic drawing, illustrating as non-limiting examples, two possible embodiments of the prosthesis to which it relates.

Figure 1:
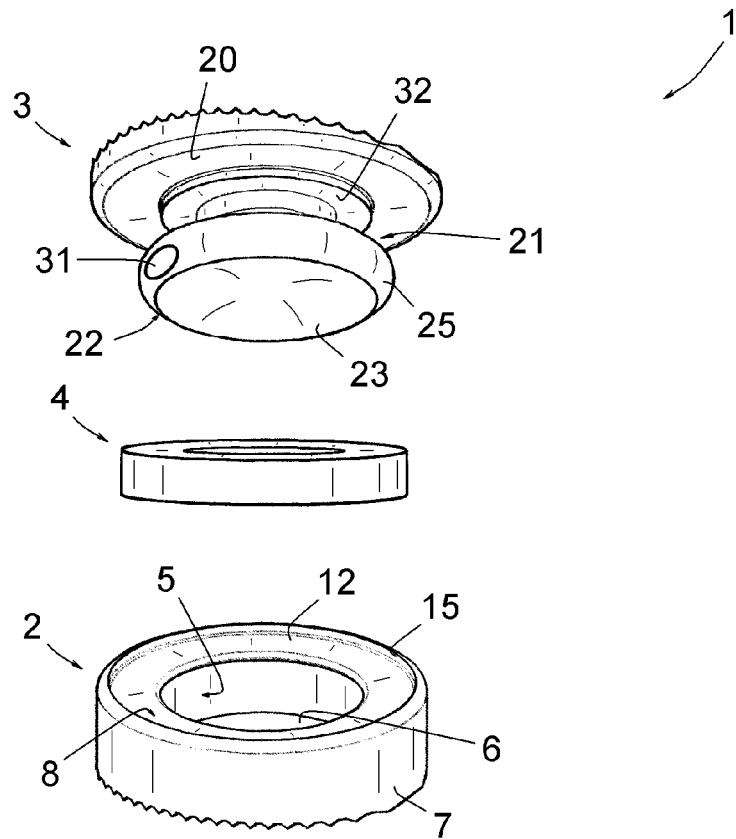
FIG. 1 is a perspective view, before assembly, according to a first embodiment.
Figure 2:
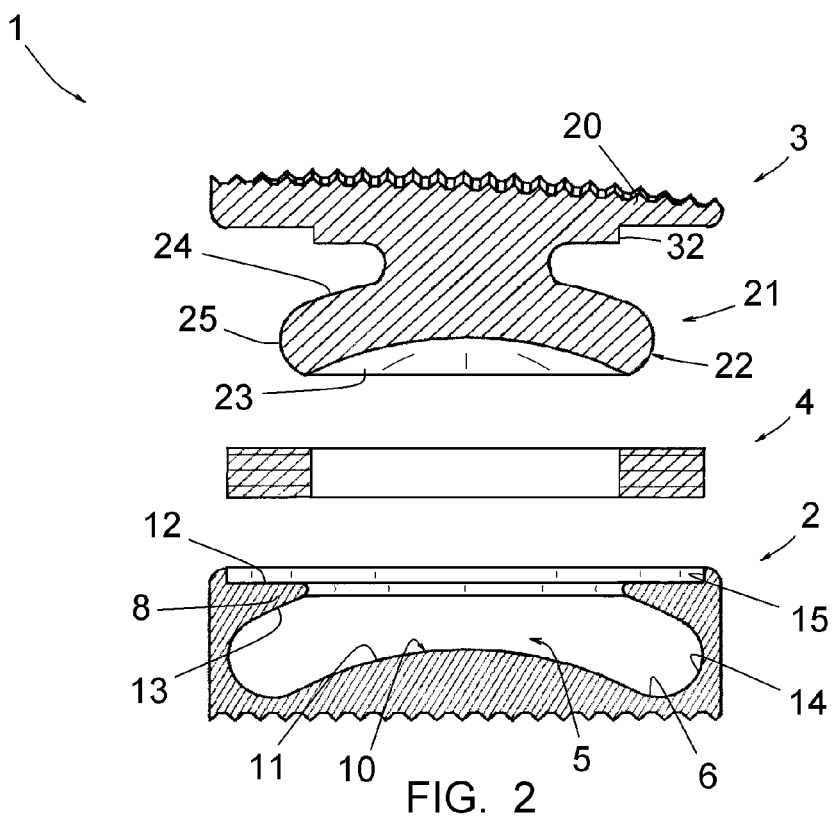
FIG. 2 is a side view thereof, as a sectional view passing through its axis.

For the sake of simplification, the portions or components of an embodiment which are found in an identical or similar way in the other embodiment will be identified by the same numerical references and will not be described again.

DETAILED DESCRIPTION OF THE INVENTION

FIGS. 1-6 illustrate a vertebral disc prosthesis 1 notably for cervical vertebrae, comprising two components 2, 3 intended to be connected to the respective vertebral plates and a ring 4 in an elastically deformable material.

The component 2, which is the lower component in the illustrated example, delimits a housing, i.e. comprises a bottom 6, a peripheral wall 7 and at a distance from the bottom 6, an edge 8 extending radially inwards. The assembly is formed into a part of strong material, notably in ceramic or biocompatible metal.

The bottom 6 has a central convex boss 10 and with the shape of a spherical cap, forming a first articular surface 11.

The edge 8 forms, on the side opposite to the bottom 6, a peripheral supporting surface 12 and, on the side turned towards the bottom 6, a second articular surface 13. The first articular surface 11 is connected to the second articular surface 13 through a rounded peripheral area 14.

The component 2 further comprises, at the border of the supporting surface 12, an outer edge 15 extending over the whole of the periphery of the supporting surface 12. As illustrated, this edge 15 has an inner diameter slightly larger than the outer diameter of the ring 4, so that this ring 4 comes into close proximity to this edge 15 when, in the mounting position, it is placed on the supporting surface 12. The edge 15 in this position thus performs lateral retention of the ring 4.

The component 3 comprises a plate 20 intended to come into contact with the vertebral plate of the relevant vertebra and a central pin 21 with a widened head 22, the assembly being formed in a piece of resistant material, notably in ceramic or in biocompatible metal.

The head 22 forms at its free end, a third articular surface 23 of a concave shape and as a spherical cap, able to cooperate with the first articular surface 11. On its side turned to the side of the plate 20, it forms a fourth articular surface 24 able to cooperate with the second articular surface 13.

The head 22 also has a rounded peripheral face 25 connected to the second and fourth articular surfaces 23, 24 through rounded connecting areas.

The head 22 further has a non-circular shape resulting from the arrangement on it of two side flats 31. This non-circular shape enables this head 22 to be engaged into the housing 5 delimited by the component 2 when the component 3 is found in a determined angular position relatively to this component 2; but preventing the this head 22 from coming free of out of this housing 5 in any other angular position of the components 2 and 3.

The component 3 further comprises a boss 32 coaxial with the pin 21, the outer diameter of which is slightly less than the inner diameter of the component 4, so that the component 4 may be fittedly engaged around this boss 32.

The housing 5 and the head 22 are mutually dimensioned so that both components 2, 3 are mobile laterally with respect to each other and axially with respect to each other, i.e. along the axis of said main pin 21 as this is described with reference to FIGS. 2-6.

Figure 3:
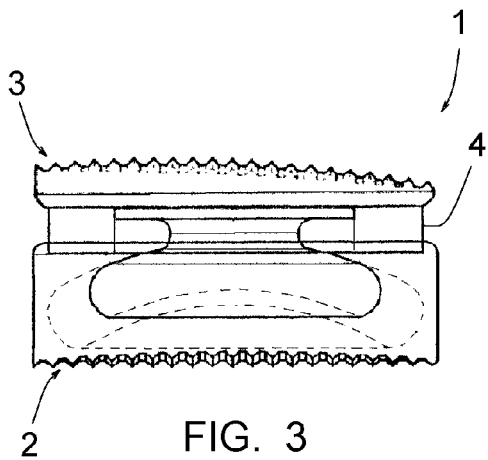
FIGS. 3-6 are side views thereof in four different relative positions of two components which it comprises.

The ring 4 may be formed in an elastomeric material, or may have an inflatable structure or it may be formed in a woven material. It may also be formed by one or more Belleville washers in metal or polymeric material. It is interposed between the supporting surface 12 and the plate 20 and as shown in FIG. 3, it normally maintains said second and fourth articular surfaces 13, 24 in contact with each other.

Figure 4:
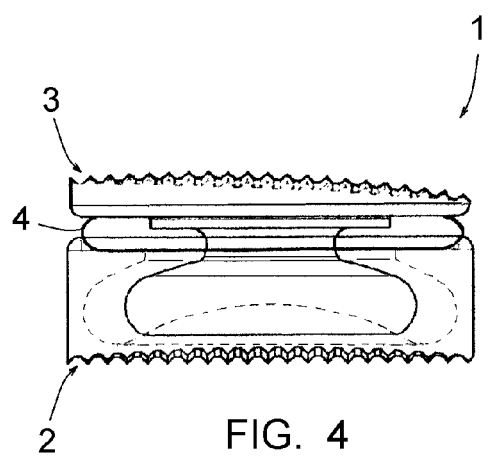
Figure 5:
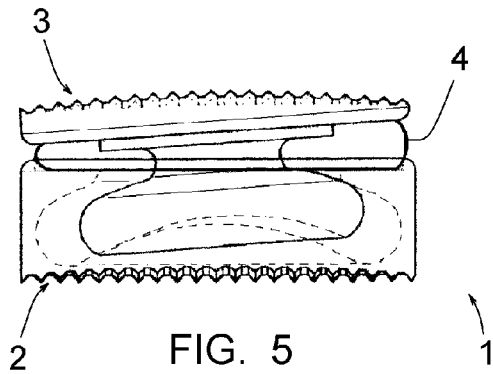
Figure 6:
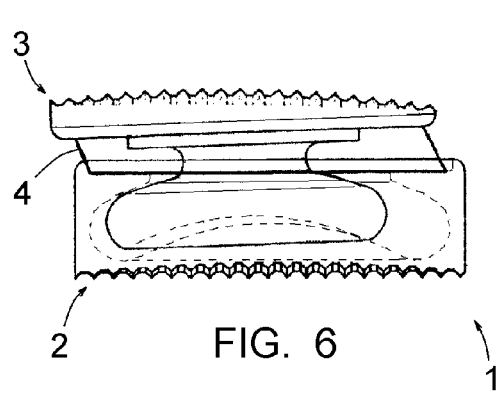

In the case of force being exerted axially on the prosthesis, as shown in FIG. 4, the ring 4 is elastically compressed within the limit of the coming of said first and third articular surfaces 11, 23 into mutual contact. This compression damps this movement of the components 2 and 3 and is limited by this contacting, thereby eliminating the risk of an excessive stress being exerted on the ring 4, capable of leading to deterioration of the latter.

In the case of a force being exerted axially but on one side of the prosthesis 1 (cf. FIG. 5), the ring 4 is only compressed on this side; it thereby allows the first and third articular surfaces 11, 23 to come into contact on this same side but, on the opposite side, it maintains the contact between said second and fourth articular surfaces 13, 24. The surfaces in contact thereby remain extensive and the deformation undergone by the ring 4 remains limited.

In the case of a force tending to displace a component 2, 3 in translation relatively to the other component 3, 2 in a transverse direction relatively to the vertebrae (cf. FIG. 6), the ring 4 allows the second and fourth articular surfaces 13, 24 to slide on each other on the side opposite to the one on which said force is exerted, while allowing contact of the first and third articular surfaces 11, 23 on the side on which said force is exerted. Here also, the articular surfaces 11, 13, 23, 24 in contact remain large and the deformation of the ring 4 only occurs within the limits allowed by the possible displacement of the first and second components 2, 3 relatively to each other. The edge 15 and the boss 32 prevent the risk of displacement of the ring 4 relatively to the components 2 and 3.

Figure 7:
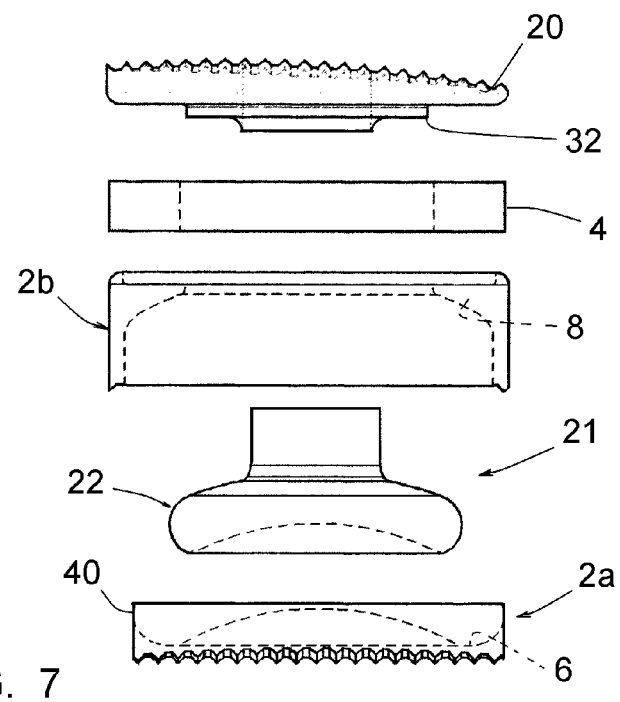
FIG. 7 is a side view thereof, before assembly, according to a second embodiment.

FIG. 7 shows an alternative embodiment in which the component 2 is in two portions 2a, 2b, a portion 2a comprising the bottom 6 and a peripheral edge 40 for assembly to the other portion 2b, and the other portion 2b comprising the peripheral wall 7 and the edge 8.

The pin is not firmly attached to the plate 20 upon placing the ring 4 and is firmly attached to this plate 20 once this placement has been achieved. The portions 2a, 2b are then assembled and attached to each other in order to form the component 2.

This embodiment enables the ring 4 to be placed between the plate 20 and the head 22 when this ring is not stretchable circumferentially, or when it is not sufficiently stretchable circumferentially in order to be engaged beyond the head 22, and allows the head 22 to be easily engaged into the housing 5 when both portions 2a, 2b are not assembled.

As is apparent from the foregoing, the invention provides a vertebral disc prosthesis, notably for cervical vertebrae, having determining advantages as compared with the homologous prostheses of the prior art, in particular that of allowing continuity of the articular surfaces to be achieved regardless of the force exerted on the prosthesis, with permanently two articular surfaces in contact. Less wear of the articular surfaces and perfect restoration of the movement of the natural joint result therefrom.

The invention was described above with reference to different embodiments given purely as examples. It is obvious that it is not limited to these embodiments but it extends to all the embodiments covered by the appended claims herein.

The invention claimed is:

1. A vertebral disc prosthesis for cervical vertebrae comprising:
   a first component and a second component intended to be connected to respective vertebral plates which are jointed to each other,
   wherein the first component comprises a bottom, a peripheral wall and, at a distance from said bottom, an edge extending inwards, which delimit between them a single central housing, said bottom forming a first articular surface, and said edge forming, on the side opposite to said bottom, a peripheral supporting surface and, on a side turned towards said bottom, a second articular surface;
   wherein the second component comprises a plate intended to come into contact with the vertebral plate of the relevant vertebra and a single central pin with a widened head, this head forming, at a free end, a third articular surface able to cooperate with said first articular surface, and, on a side turned to the side of said plate, a fourth articular surface able to cooperate with said second articular surface;
   wherein said housing and said head are mutually dimensioned so that the first component and the second component are mobile relative to each other, sideways, perpendicularly to the axis of said central pin, and axially relative to each other, along the axis of this central pin; and
   wherein the prosthesis comprises at least one third component made of an elastically deformable material, interposed between said peripheral supporting surface of the first component and said plate of the second component, each third component maintains said second and fourth articular surfaces in contact with each other, each third component being able to be compressed so that said first and third articular surfaces come into contact with each other;
   when a force is exerted axially on a first side of the prosthesis, each third component is only compressed on the first side of the prosthesis allowing the first and the third articular surfaces to come into contact on the first side of the prosthesis and the second and fourth articular surfaces to come into contact on a second side of the prosthesis; and
   when the force tends to displace the first component or the second component in a translation relative to the other component in a transverse direction relative to the vertebrae, each third component allows the second and fourth articular surfaces to slide on each other on the side opposite to the one on which said force is exerted, while allowing contact of the first and the third articular surfaces on the side on which said force is exerted.

2. The prosthesis according to claim 1, wherein each third component is a ring-shaped device.

3. The prosthesis according to claim 1 wherein said first component comprises, at the border of said supporting surface, an outer retaining edge dimensioned in order to perform lateral retention of each third component.

4. The prosthesis according to claim 3, wherein said outer retaining edge extends over the entire periphery of said supporting surface.

5. The prosthesis according to claim 2 wherein said second component comprises on the side of said plate, a boss coaxial with said pin, dimensioned so as to fittedly receive the elastically deformable component.

6. The prosthesis according to claim 1 wherein said first articular surface is convex and in the shape of a spherical cap, said third articular surface being concave and with a complementary shape to this first articular surface.

7. The prosthesis according to claim 1 wherein the head of the pin has a rounded peripheral face, connected to said second and fourth articular surfaces through rounded connecting areas, and in that said first articular surface is connected to said second articular surface through a rounded peripheral area.

8. The prosthesis according to claim 1 wherein said first and second components are made of ceramic.

9. The prosthesis according to claim 1 wherein said first component is in two portions, allowing the head of said pin to be easily engaged into the housing delimited by this component when both of these portions are not assembled, and retaining this head in this housing when they are assembled.

10. A vertebral disc prosthesis for cervical vertebrae comprising:
- a first component and a second component intended to be connected to respective vertebral plates which are jointed to each other,
- wherein the first component comprises a bottom, a peripheral wall and, at a distance from said bottom, an edge extending inwards, which delimit between them a single central housing, said bottom forming a first articular surface, and said edge forming, on the side opposite to said bottom, a peripheral supporting surface and, on a side turned towards said bottom, a second articular surface;
- wherein the second component comprises a plate intended to come into contact with the vertebral plate of the relevant vertebra and a single central pin with a widened head, this head forming, at a free end, a third articular surface able to cooperate with said first articular surface, and, on a side turned to the side of said plate, a fourth articular surface able to cooperate with said second articular surface;
- wherein said housing and said head are mutually dimensioned so that the first component and the second component are mobile relative to each other, sideways, perpendicularly to the axis of said central pin, and axially relative to each other, along the axis of this central pin; and the prosthesis further comprises:
- at least one third component made of an elastically deformable material interposed between said peripheral supporting surface of the first component and said plate of the second component, each third component maintains said second and fourth articular surfaces in contact with each other, each third component being able to be compressed so that said first and third articular surfaces come into contact with each other;
- a boss located coaxial with the central pin, the boss having an outer diameter slightly less than an inner diameter of the third component;
- wherein the third component tightly engages around the boss;
- when a force is exerted axially on a first side of the prosthesis, each third component is only compressed on the first side of the prosthesis allowing the first and the third articular surfaces to come into contact on the first side of the prosthesis and the second and fourth articular surfaces to come into contact on a second side of the prosthesis; and
- when the force tends to displace, the first component or the second component in a translation relative to the other component in a transverse direction relative to the vertebrae, each third component allows the second and fourth articular surfaces to slide on each other on the side opposite to the one on which said force is exerted, while allowing contact of the first and the third articular surfaces on the side on which said force is exerted.

* * * * *